United States Patent
Lygin et al.

(10) Patent No.: US 10,232,353 B2
(45) Date of Patent: Mar. 19, 2019

(54) GOLD-BASED CATALYST FOR THE OXIDATIVE ESTERIFICATION OF ALDEHYDES TO OBTAIN CARBOXYLIC ESTERS

(71) Applicants: Alexander Lygin, Griesheim (DE); Steffen Krill, Muehltal (DE); Matthias Groemping, Darmstadt (DE); Andreas Tepperis, Bad Koenig (DE)

(72) Inventors: Alexander Lygin, Griesheim (DE); Steffen Krill, Muehltal (DE); Matthias Groemping, Darmstadt (DE); Andreas Tepperis, Bad Koenig (DE)

(73) Assignee: Evonik Röhm GmbH, Darmstadt (DE)

( * ) Notice: Subject to any disclaimer, the term of this patent is extended or adjusted under 35 U.S.C. 154(b) by 0 days.

(21) Appl. No.: 15/543,291

(22) PCT Filed: Dec. 29, 2015

(86) PCT No.: PCT/EP2015/081338
§ 371 (c)(1),
(2) Date: Jul. 13, 2017

(87) PCT Pub. No.: WO2016/113106
PCT Pub. Date: Jul. 21, 2016

(65) Prior Publication Data
US 2018/0001307 A1    Jan. 4, 2018

(30) Foreign Application Priority Data
Jan. 16, 2015    (EP) .................................... 15151466

(51) Int. Cl.
| | | |
|---|---|---|
| *B01J 23/02* | (2006.01) | |
| *B01J 23/04* | (2006.01) | |
| *B01J 23/10* | (2006.01) | |
| *B01J 23/14* | (2006.01) | |
| *B01J 23/18* | (2006.01) | |
| *B01J 23/34* | (2006.01) | |
| *B01J 23/52* | (2006.01) | |
| *B01J 23/66* | (2006.01) | |
| *B01J 23/68* | (2006.01) | |
| *B01J 23/89* | (2006.01) | |
| *B01J 35/00* | (2006.01) | |
| *B01J 35/02* | (2006.01) | |
| *B01J 35/08* | (2006.01) | |
| *B01J 37/02* | (2006.01) | |
| *B01J 37/04* | (2006.01) | |
| *C07C 67/39* | (2006.01) | |
| *C07C 69/54* | (2006.01) | |

(52) U.S. Cl.
CPC .............. *B01J 23/52* (2013.01); *B01J 23/02* (2013.01); *B01J 23/04* (2013.01); *B01J 23/10* (2013.01); *B01J 23/14* (2013.01); *B01J 23/18* (2013.01); *B01J 23/34* (2013.01); *B01J 23/66* (2013.01); *B01J 23/681* (2013.01); *B01J 23/688* (2013.01); *B01J 35/006* (2013.01); *B01J 35/0006* (2013.01); *B01J 35/008* (2013.01); *B01J 35/0013* (2013.01); *B01J 35/0033* (2013.01); *B01J 35/026* (2013.01); *B01J 35/08* (2013.01); *B01J 37/0207* (2013.01); *B01J 37/0213* (2013.01); *B01J 37/0236* (2013.01); *B01J 37/0244* (2013.01); *B01J 37/04* (2013.01); *C07C 67/39* (2013.01); *B01J 23/8946* (2013.01); *B01J 2523/00* (2013.01)

(58) Field of Classification Search
CPC ... B01J 23/02; B01J 23/04; B01J 23/10; B01J 23/14; B01J 23/18; B01J 23/34; B01J 23/52; B01J 23/66; B01J 23/681; B01J 23/688; B01J 35/0006; B01J 35/0013; B01J 35/0033; B01J 35/006; B01J 35/008; B01J 35/026; B01J 35/08; B01J 37/0207; B01J 37/0213; B01J 37/0236; B01J 37/0244; B01J 37/04; B01J 23/8946; B01J 2523/00; C07C 67/39
See application file for complete search history.

(56) References Cited

U.S. PATENT DOCUMENTS

| | | |
|---|---|---|
| 5,969,178 A | 10/1999 | Okamoto et al. |
| 6,040,472 A | 3/2000 | Yamamatsu et al. |
| 7,012,039 B2 | 3/2006 | Watanabe et al. |
| 2010/0249448 A1 | 9/2010 | Suzuki et al. |
| 2011/0184206 A1* | 7/2011 | Suzuki ................... B01J 23/755 560/103 |

(Continued)

FOREIGN PATENT DOCUMENTS

| | | |
|---|---|---|
| EP | 1 393 800 A1 | 3/2004 |
| EP | 2 177 267 A1 | 4/2010 |
| EP | 2 210 664 A1 | 7/2010 |

OTHER PUBLICATIONS

International Search Report dated Jun. 2, 2016 in PCT/EP2015/081338 filed Dec. 29, 2015.

(Continued)

*Primary Examiner* — Pancham Bakshi
*Assistant Examiner* — Mark R Luderer
(74) *Attorney, Agent, or Firm* — Oblon, McClelland, Maier & Neustadt, L.L.P.

(57) ABSTRACT

Catalysts for oxidative esterification can be used, for example, for converting (meth)acrolein to methyl (meth)acrylate. The catalysts are especially notable for high mechanical and chemical stability even over very long time periods, including activity and/or selectivity relatively in continuous operation in media having even a small water content.

20 Claims, No Drawings

(56) References Cited

U.S. PATENT DOCUMENTS

2013/0172599 A1    7/2013   Suzuki et al.

OTHER PUBLICATIONS

European Search Report dated Jul. 22, 2015 in European Application 15151466.8 filed Jan. 16, 2015.
U.S. Appl. No. 14/773,602, filed Sep. 8, 2015, US 2016-0031786 A1, Torsten Balduf et al.
U.S. Appl. No. 14/784,320, filed Oct. 14, 2015, US 2016-0068464 A1, Steffen Krill et al.
U.S. Appl. No. 15/037,212, filed May 17, 2016, US 2016-0280628 A1, Steffen Krill et al.
U.S. Appl. No. 15/515,682, filed Mar. 30, 2017, Steffen Krill et al.

* cited by examiner

GOLD-BASED CATALYST FOR THE OXIDATIVE ESTERIFICATION OF ALDEHYDES TO OBTAIN CARBOXYLIC ESTERS

FIELD OF THE INVENTION

The present invention relates to novel catalysts for oxidative esterification, by means of which, for example, (meth)acrolein can be converted to methyl (meth)acrylate. The catalysts of the invention are especially notable for high mechanical and chemical stability even over very long periods. This especially relates to an improvement over prior art catalysts which lose activity and/or selectivity relatively quickly in continuous operation in media having even a small water content.

PRIOR ART

The catalytic oxidative esterification of aldehydes for preparation of carboxylic esters is described extensively in the prior art. For example, it is possible in this way to prepare methyl methacrylate very efficiently from methacrolein (MAL) and methanol. U.S. Pat. No. 5,969,178 and U.S. Pat. No. 7,012,039 in particular describe a process for continuously preparing MMA from isobutene or tert-butanol. This process has the following steps: 1) oxidation of isobutene or tert-butanol to methacrolein and 2) direct oxidative esterification of MAL with methanol to give MMA with a Pd—Pb catalyst on an oxidic support.

However, all the catalysts known from the prior art are sensitive particularly to aqueous media over the course of prolonged service lives. For example, EP 1 393 800 describes good activities and selectivities, but at the same time no information is given as to the lifetime of the catalysts. These catalysts are gold-containing catalysts, especially gold nanoparticles having an average diameter of less than 6 nm on a support. The selectivities for MMA at a content of 4.5% by weight of Au are reported to be up to 93%, and the space-time yield is reported to be up to 50.7 mol of MMA/kg cat.*h. The pH of the gold-containing solution in the catalyst production is in the range from 5 to 10, preferably between 6 and 9.

U.S. Pat. No. 6,040,472 describes alternative catalysts, but these lead only to inadequate activities and selectivities for MMA by comparison. In this case, the catalysts are Pd/Pb-containing catalysts having a shell structure. The selectivities for MMA are reported to be up to 91%, and the space-time yield is reported to be up to 5.3 mol.

EP 2 177 267 and EP 2 210 664 describe nickel-containing catalysts with shell structure. Selectivity for MMA in the case of these catalysts is up to 97%. The space-time yield is described as 9.7 mol of MMA/kg cat.*h with a gold content in the catalyst of about 1% by weight.

US 2013/0172599, in turn, describes a silicon-containing material consisting of Si, Al and a basic third component, and also a metal having elevated acid resistance. This metal is Ni, Co, Zn or Fe. This material can be used as support for noble metal-containing catalysts. A preferred catalyst variant for the oxidative esterification of methacrolein to MMA includes an Au/NiO catalyst supported on $SiO_2$—$Al_2O_3$—MgO.

However, it is apparent from Comparative Example 2 that this catalyst loses activity with time. This is probably attributable to the adverse effect of water present in the reaction mixture.

Problem

The primary problem addressed by the present invention was that of providing for the preparation of a novel catalyst for a highly selective oxidative esterification of aldehydes to carboxylic esters. At the same time, this catalyst is to have high mechanical and chemical stability, especially in water- and carboxylic acid-containing mixtures, and possess longer retention of activity (productivity) and selectivity compared to the prior art.

A particular problem addressed was that this catalyst is to be suitable for the oxidative esterification of methacrolein to an alkyl methacrylate, especially to MMA.

Further problems which are not stated explicitly may become apparent from the description, the examples, the claims or the overall context of the present invention.

Solution

The stated problems were solved with the aid of novel hydrolysis-resistant catalysts. These catalysts of the invention are in the form of particles and can be used over a long period in the oxidative esterification of aldehydes to carboxylic esters. The catalysts of the invention are characterized in that they have the following constituents:

a) 0.01 to 10 mol %, preferably 0.05 to 2 mol %, of gold,
b) 40 to 94 mol % of silicon,
c) 3 to 40 mol % of aluminium and
d) 2 to 40 mol %, preferably 2 to 30 mol %, of at least one further element selected from alkali metals, alkaline earth metals, rare earth metals, Ti, Zr, Cu, Mn, Pb, Sn or Bi; components b) to d) are present here as oxides. The stated amounts listed for components a) to d) relate to 100 mol % of the composition of the catalyst not including oxygen. This statement of the composition with exclusion of the oxygen present in the oxides is appropriate since some of the elements have distinctly different oxidation states or, for example, mixed oxides may also be present. Preferably, the catalyst except for the oxygen consists of components a) to d).

In addition, the catalyst has a shell structure composed of a core and at least one shell, preferably of a core and one or two shells. Component a) is part of a shell to an extent of at least 80% of the total mass of component a), preferably to an extent of at least 90% and more preferably completely.

In a preferred variant, the catalyst includes, as well as the core and a gold-containing shell directly adjoining it, a further thin outer shell which especially consists of one or more components b) to d) and includes not more than small amounts of component a). This shell serves to further prolong the service life by the reduction of abrasion of component a) under high mechanical stress.

"Shell structure" in this case means that the core in principle has a more or less intrinsically homogeneous structure, whereas the shell, i.e. a region surrounding the core, has a structure distinguishable therefrom. "More or less homogeneous" means here that there can quite possibly be local differences, for example in the form of oxidic nanocrystals, within the core or a shell, but such nanophases are distributed homogeneously over the entire core or entire shell. One example is the gold in the catalytically active shell, which is distributed homogeneously over this shell in the form of nanoparticles.

More particularly, "shell structure" means a distribution of the active component (Au) in the entire catalyst body in which the majority of the gold atoms is present close to the surface, and hence within a region which, viewed from the outside, makes up less than 50% of the particle radius, and hence they are not distributed homogeneously over the entire catalyst body.

It should also be pointed out that the boundary between the core and a shell or between two shells need not be sharp, but may quite possibly be in the form of a gradient with varying composition. For example, the concentration of gold nanoparticles, viewed from the core, may increase from the inside outward. This arises merely from the fact that the particles of the invention generally have a relatively high porosity. At the same time, in less preferred embodiments with more than one shell, wherein the gold particles are concentrated in an outer shell and a gradient is present in the gold particle distribution, according to the invention, less than 20%, preferably less than 10% and more preferably no gold particles are present within the inner at least 50% of the total particle radius, where the latter may include not only the core but also inner shells having a low or zero gold content.

A further essential feature of the catalysts of the invention is that they have a point of zero charge (referred to hereinafter as PZC value) between 7 and 11. An exact definition and methods for determination of the PZC value can be found, for example, in Powder technology, 103, 1999, 30-36. It is explained here that the PZC value is one of the most important characteristics of an oxidic surface of a solid present in a liquid medium. The PZC value can be regarded as an analogue of the pH of a liquid, especially of an aqueous medium, when the sum total of the negative and positive charges at the oxidic surface is balanced. Thus, the charge of an oxidic surface is negative when the pH of the surrounding liquid is greater than the PZC value and, conversely, the surface charge is positive when the PZC value is greater than the pH of the surrounding liquid medium. Suitable methods for determining the PZC value, especially for particles having a diameter less than 20 μm, are the determination of a zeta potential and electrophoretic micromobility. Another alternative and much simpler method of determination which is independent of the particle size is that of simply determining the pH of the surrounding, generally aqueous medium in which the oxidic particles are present in concentrated suspension. In this way, an approximate PZC value sufficient for the performance of the present invention is obtained, by means of which good compatibility of different particles with one another is possible.

With this invention, it has been found that, surprisingly, the abovementioned problems are solved especially by a particular combination of gold as component a), oxides of silicon as component b) and of aluminium as component c), and one or more oxides selected preferably from the following elements: Li, Na, K, Rb, Cs, Be, Mg, Ca, Sr, Ba, Sc, Y, Ti, Zr, Cu, Mn, Pb, Sn, Bi or lanthanoids having atomic numbers 57 to 71 as component d). This surprisingly enables, in particular, the retention of activity and selectivity of the catalyst used for the oxidative esterification over a long period, without any noticeable reduction therein. More preferably, component d) is Mg, Ce, La, Y, Zr, Mn, Pb, Bi and/or mixtures of these elements.

In this context, it has especially been found that, surprisingly, the acidity/basicity of the catalyst plays a crucial role for the attainment of the best catalyst performance. If the catalyst is too acidic, there is increased formation of acetals as a by-product in the reaction mixture of the oxidative esterification, i.e. the raw materials of the oxidative esterification, and the selectivity is thus distinctly lowered. If the catalyst, in contrast, is too basic, the Michael adducts of alcohols having double bonds, as present, for example, in the meth-acrolein (MAL), are formed in the reaction mixture, and the selectivity is thus likewise distinctly lowered. According to the invention, the catalyst needs a somewhat basic surface. A measure of the acidity/basicity of a catalyst surface can be taken to be the PZC value thereof.

Preferably, the catalyst particles have a mean diameter between 10 and 200 μm, more preferably between 20 and 120 μm, and at the same time a spherical shape. At the same time or independently thereof, component a) is preferably in the form of particles having a mean diameter between 2 and 10 nm.

As well as the catalysts described for an oxidative esterification, another part of the present invention is in particular a process for preparing catalysts for an oxidative esterification. This process for producing catalyst particles is characterized in that a basic mixed oxide support having a PZC value between 8 and 12 and a mean diameter between 10 and 200 μm, consisting of b) 40 to 94 mol % of silicon, c) 3 to 40 mol % of aluminium and d) 2 to 40 mol % of at least one further element selected from alkali metals, alkaline earth metals, rare earth metals, Ti, Zr, Cu, Mn, Pb, Sn or Bi, where components b) to d) are present as oxides and the stated amounts of components a) to d) relate to 100 mol % of the composition of the catalyst without oxygen, is admixed with a gold-containing solution which forms component a) having a pH between 0.5 and 5.0. The gold-containing solution may especially be an aqueous solution of tetrachloroauric acid. This solution may optionally also contain soluble salts of other elements from b), c) and/or d).

The way in which the gold-containing active component is applied to the support composed of components b), c) and d) is crucial in accordance with the invention. In this context, both the basicity of the support used and the acidity of the gold-containing solution play a major role. The combination of these two factors enables synthesis of a catalyst with shell structure having high activity, selectivity and hydrolysis stability and long service lives.

The acidity of the gold-containing solution has a particular influence on the formation of various species of gold(III) complex ions in the solution (see, for example, Geochimica et Cosmochimica Acta Vol. 55, pp. 671-676) and ultimately on the nature of the bond to the surface of the support. In many references, a pH of the gold-containing solution around 7 is preferred (see, for example, EP 1 393 800). According to the invention, it has been found that, surprisingly, the pH range between 0.5 and 5.0 proved to be the best condition for the catalyst performance of the catalyst produced by means of this process.

In a particular variant of this process, the gold-containing solution contains not only the gold compound but at least one additional compound. This compound in turn includes components b), c) and/or d) in ionic form. With this variant, an additional protective layer for gold particles can arise, which is additionally beneficial for a longer service life of the catalyst. Component b) in ionic form means in this case that silicates, for example sodium silicates or ammonium silicates, which are converted to silicon oxides at a later stage in an optional thermal sintering or calcination, are present in the solution. Components c) or d) in ionic form mean the corresponding water-soluble salts, for example aluminium nitrate, aluminium sulphate, etc.

After the production of the particles described, isolation, for example by means of filtration, and further purification, with particular preference, they are finally calcined. This can be accomplished, for example, at temperatures between 300 and 600° C.

As well as the catalysts described and the process for production thereof described, the present invention also provides for the use of such a catalyst of the invention or catalyst produced in accordance with the invention in the reaction of (meth)acrolein with oxygen and a monofunctional alcohol to give an alkyl (meth)acrylate. The brackets in (meth)acrolein mean that this raw material may be either acrolein or methacrolein. Correspondingly, alkyl (meth)acrylate means either alkyl acrylate or alkyl methacrylate. This alkyl group is determined by the alcohol used.

Preferably, in the case of this use, methacrolein is reacted with oxygen and methanol in the presence of the catalyst of the invention to give MMA.

Alternatively, in the case of this use, it is also possible to react (meth)acrolein with oxygen and a di-, tri- or tetrafunctional alcohol to give a hydroxyalkyl (meth)acrylate and di-, tri- or tetra(meth)acrylate. The latter compounds are known as crosslinkers. A particularly preferred example of a difunctional alcohol is ethylene glycol.

Particular preference is given to conducting the oxidative esterification continuously in the presence of the catalyst of the invention. Most preferably, the catalyst is employed in suspension form (as a slurry) in a stirred reactor during the oxidative esterification.

EXAMPLES

PZC Measurement

Powder material (3.0 g) is suspended in 7.5 ml of a 0.1% by weight solution of NaCl in demineralized water and stirred with a magnetic stirrer (100 rpm). After stirring at room temperature for 15 min, the pH of the suspension is measured with a pH probe. This value is referred to hereinafter as PZC.

Production of a Preformed Support

Example 1

A 250 ml beaker is initially charged with 21.35 g of $Mg(NO_3)_2*6H_2O$ and 31.21 g of $Al(NO_3)_3*9H_2O$ which are dissolved in 41.85 g of demineralized water while stirring on a magnetic stirrer. Thereafter, 1.57 g of 60% by weight $HNO_3$ are added while stirring. 166.67 g of silica sol (Köstrosol 1530AS from Bad Köstritz) are weighed into a 500 ml three-neck flask and cooled to 15° C. while stirring. 2.57 g of 60% by weight $HNO_3$ are added gradually to the sol while continuing to stir. At 15° C., the nitrate solution is added to the sol within 45 min while stirring. After the addition, the mixture is heated to 50° C. within 30 min and stirred at this temperature for a further 24 h. After this time, the mixture is dried in a thin layer on a preheated dish at 130° C. in a drying cabinet and then crushed with a mortar and pestle to give a fine powder. The dried powder is heated in a thin layer in a Naber oven to 300° C. over the course of 2 h, kept at 300° C. for 3 h, heated to 600° C. over the course of 2 h and kept at 600° C. for a further 3 h. The PZC of this material was 9.81.

Example 2

A 250 ml beaker is initially charged with 32.03 g of $Mg(NO_3)_2*6H_2O$ and 31.21 g of $Al(NO_3)_3*9H_2O$ together, which are dissolved in 41.85 g of demineralized water while stirring with a magnetic stirrer. Thereafter, 1.57 g of 60% by weight $HNO_3$ are added while stirring. 166.67 g of silica sol (Köstrosol 1530AS from Bad Köstritz) are weighed into a 500 ml three-neck flask and cooled to 15° C. while stirring. 2.57 g of 60% by weight $HNO_3$ are added gradually to the sol with stirring. At 15° C., the nitrate solution is added to the sol over the course of 45 min while stirring. After the addition, the mixture is heated to 50° C. within 30 min and stirred at this temperature for a further 24 h. After this time, the mixture is dried in a thin layer on a preheated dish at 130° C. in a drying cabinet, then crushed with a mortar and pestle to give a fine powder. The dried powder is heated in a thin layer in a Naber oven to 300° C. within 2 h, kept at 300° C. for 3 h, heated to 600° C. within a further 2 h and finally kept at 600° C. for a further 3 h. The PZC of this material was 9.36.

Example 3

A 250 ml beaker is initially charged with 10.68 g of $Mg(NO_3)_2*6H_2O$ and 31.21 g of $Al(NO_3)_3*9H_2O$ together, which are dissolved in 41.85 g of demineralized water while stirring with a magnetic stirrer. Thereafter, 1.57 g of 60% by weight $HNO_3$ are added while stirring. 166.67 g of silica sol (Köstrosol 1530AS from Bad Köstritz) are weighed into a 500 ml three-neck flask and cooled to 15° C. while stirring. 2.57 g of 60% by weight $HNO_3$ are added gradually to the sol while stirring. At 15° C., the nitrate solution is added to the sol within 45 min while stirring. After the addition, the mixture is heated to 50° C. within 30 min and stirred at this temperature for a further 24 h. After this time, the mixture is dried in a thin layer on a preheated dish at 130° C. in a drying cabinet, then crushed with a mortar and pestle to give a fine powder. The dried powder is heated in a thin layer in a Naber oven to 300° C. over the course of 2 h, kept at 300° C. for 3 h, heated to 600° C. within a further 2 h and finally kept at 600° C. for a further 3 h. The PZC of this material was 7.91.

Production of a Doped Support

Examples 4 to 13 and Comparative Example 1

Comparative Example 1 (Sn)

$SnCl_2*2H_2O$ (440 mg, 1.95 mmol) was dissolved in 5 g of distilled methanol and the solution was mixed and shaken vigorously with 10 g of the above-described preformed $SiO_2$—$Al_2O_3$—MgO support from Example 1. The support thus obtained, having a dry appearance, was dried in a thin layer in a drying cabinet at 105° C. for 10 h, then finely crushed in a mortar and pestle and heated in a thin layer in a Naber oven to 300° C. within 2 h, kept at 300° C. for 3 h, heated to 600° C. within a further 2 h and finally kept at 600° C. for a further 3 h. The PZC of this material was 6.85.

Example 4 (Bi)

$Bi(NO_3)_3*5H_2O$ (947 mg, 1.95 mmol) was dissolved in 5 g of demineralized water with addition of 2.9 g of 60% by weight $HNO_3$ and the solution was mixed and shaken vigorously with 10 g of the above-described preformed $SiO_2$—$Al_2O_3$—MgO support from Example 1. The support thus obtained, having a dry appearance, was dried in a thin layer in a drying cabinet at 105° C. for 10 h, then finely crushed in a mortar and pestle and heated in a thin layer in a Naber oven to 300° C. within 2 h, kept at 300° C. for 3 h, heated to 600° C. within 2 h and kept at 600° C. for a further 3 h. The PZC of this material was 9.21.

Example 5 (Mn)

$Mn(NO_3)_2*4H_2O$ (494 mg, 1.95 mmol) was dissolved in 5 g of demineralized water and the solution was mixed and

Example 6 (Ce)

Ce(NO$_3$)$_3$*6H$_2$O (848 mg, 1.95 mmol) was dissolved in 5 g of demineralized water and the solution was mixed and shaken vigorously with 10 g of the above-described preformed SiO$_2$—Al$_2$O$_3$—MgO support from Example 1. The support thus obtained, having a dry appearance, was dried in a thin layer in a drying cabinet at 105° C. for 10 h, then finely crushed in a mortar and pestle and heated in a thin layer in a Naber oven to 300° C. within 2 h, kept at 300° C. for 3 h, heated to 600° C. within 2 h and finally kept at 600° C. for 3 h. The PZC of this material was 9.56.

Example 7 (Zr)

ZrO(NO$_3$)$_2$*6H$_2$O (663 mg, 1.95 mmol) was dissolved in 5 g of demineralized water and the solution was mixed and shaken vigorously with 10 g of the above-described preformed SiO$_2$—Al$_2$O$_3$—MgO support from Example 1. The support thus obtained, having a dry appearance, was dried in a thin layer in a drying cabinet at 105° C. for 10 h, then finely crushed in a mortar and pestle and heated in a thin layer in a Naber oven to 300° C. within 2 h, kept at 300° C. for 3 h, heated to 600° C. within 2 h and finally kept at 600° C. for 3 h. The PZC of this material was 8.90.

Example 8 (Pb)

Pb(NO$_3$)$_2$ (647 mg, 1.95 mmol) was dissolved in 5 g of demineralized water and the solution was mixed and shaken vigorously with 10 g of the above-described preformed SiO$_2$—Al$_2$O$_3$—MgO support from Example 1. The support thus obtained, having a dry appearance, was dried in a thin layer in a drying cabinet at 105° C. for 10 h, then finely crushed in a mortar and pestle and heated in a thin layer in a Naber oven to 300° C. within 2 h, kept at 300° C. for 3 h, heated to 600° C. within 2 h and finally kept at 600° C. for 3 h. The PZC of this material was 9.35.

Example 9 (Al)

Al(NO$_3$)$_3$*9H$_2$O (734 mg, 1.95 mmol) was dissolved in 5 g of demineralized water and the solution was mixed and shaken vigorously with 10 g of the above-described preformed SiO$_2$—Al$_2$O$_3$—MgO support from Example 1. The support thus obtained, having a dry appearance, was dried in a thin layer in a drying cabinet at 105° C. for 10 h, then finely crushed in a mortar and pestle and heated in a thin layer in a Naber oven to 300° C. in 2 h, kept at 300° C. for 3 h, heated to 600° C. in 2 h and kept at 600° C. for 3 h. The PZC of this material was 9.12.

Example 10 (Y)

Y(NO$_3$)$_3$*6H$_2$O (750 mg, 1.95 mmol) was dissolved in 5 g of demineralized water and the solution was mixed and shaken vigorously with 10 g of the above-described preformed SiO$_2$—Al$_2$O$_3$—MgO support from Example 1. The support thus obtained, having a dry appearance, was dried in a thin layer in a drying cabinet at 105° C. for 10 h, then finely crushed in a mortar and pestle and heated in a thin layer in a Naber oven to 300° C. within 2 h, kept at 300° C. for 3 h, heated to 600° C. within 2 h and finally kept at 600° C. for 3 h. The PZC of this material was 9.34.

Example 11 (La)

La(NO$_3$)$_3$*6H$_2$O (845 mg, 1.95 mmol) was dissolved in 5 g of demineralized water and the solution was mixed and shaken vigorously with 10 g of the above-described preformed SiO$_2$—Al$_2$O$_3$—MgO support. The support thus obtained, having a dry appearance, was dried in a thin layer in a drying cabinet at 105° C. for 10 h, then finely crushed in a mortar and pestle and heated in a thin layer in a Naber oven to 300° C. within 2 h, kept at 300° C. for 3 h, heated to 600° C. within 2 h and finally kept at 600° C. for 3 h. The PZC of this material was 10.20.

Example 12 (Mg)

Mg(NO$_3$)$_2$*6H$_2$O (2.0 g, 7.8 mmol) was dissolved in 5 g of demineralized water and the solution was mixed and shaken vigorously with 10 g of the above-described preformed SiO$_2$—Al$_2$O$_3$—MgO support from Example 1. The support thus obtained, having a dry appearance, was dried in a thin layer in a drying cabinet at 105° C. for 10 h, then finely crushed in a mortar and pestle and heated in a thin layer in a Naber oven to 300° C. within 2 h, kept at 300° C. for 3 h, heated to 600° C. within 2 h and finally kept at 600° C. for 3 h. The PZC of this material was 12.14.

Example 13 (Li)

LiOH (470 mg, 19.5 mmol) was dissolved in 5 g of demineralized water and the solution was mixed and shaken vigorously with 10 g of the above-described preformed SiO$_2$—Al$_2$O$_3$—MgO support from Example 1. The support thus obtained, having a dry appearance, was dried in a thin layer in a drying cabinet at 105° C. for 10 h, then finely crushed in a mortar and pestle and heated in a thin layer in a Naber oven to 300° C. within 2 h, kept at 300° C. for 3 h, heated to 600° C. within 2 h and finally kept at 600° C. for 3 h. The PZC of this material was 12.31.

Catalyst Production (Application of Au to a Doped Support)

Examples 14 to 27 and Comparative Examples 2 to 5

Comparative Example 2

A suspension of 10 g of doped support from Comparative Example 1 in 33.3 g of demineralized water was heated to 90° C. and stirred at this temperature for 15 min. Added to the suspension while stirring was a solution, previously preheated to 90° C., of HAuCl$_4$*3H$_2$O (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 8.89.

Example 14

A suspension of 10 g of doped support from Example 4 in 33.3 g of demineralized water was heated to 90° C. and stirred at this temperature for 15 min. Added to the suspension while stirring was a solution, previously preheated to 90° C., of HAuCl$_4$*3H$_2$O (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 9.09.

Example 15

A suspension of 10 g of doped support from Example 5 in 33.3 g of demineralized water was heated to 90° C. and stirred at this temperature for 15 min. Added to the suspension while stirring was a solution, previously preheated to 90° C., of HAuCl$_4$*3H$_2$O (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 8.72.

Example 16

A suspension of 10 g of doped support from Example 6 in 33.3 g of demineralized water was heated to 90° C. and stirred at this temperature for 15 min. Added to the suspension while stirring was a solution, previously preheated to 90° C., of HAuCl$_4$*3H$_2$O (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 8.92.

Example 17

A suspension of 10 g of doped support from Example 7 in 33.3 g of demineralized water was heated to 90° C. and stirred at this temperature for 15 min. Added to the suspension while stirring was a solution, previously preheated to 90° C., of HAuCl$_4$*3H$_2$O (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 8.87.

Example 18

A suspension of 10 g of doped support from Example 8 in 33.3 g of demineralized water was heated to 90° C. and stirred at this temperature for 15 min. Added to the suspension while stirring was a solution, previously preheated to 90° C., of HAuCl$_4$*3H$_2$O (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 8.59.

Example 19

A suspension of 10 g of doped support from Example 9 in 33.3 g of demineralized water was heated to 90° C. and stirred at this temperature for 15 min. Added to the suspension while stirring was a solution, previously preheated to 90° C., of HAuCl$_4$*3H$_2$O (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 8.82.

Comparative Example 3

A suspension of 10 g of doped support from Example 1 in 33.3 g of demineralized water was heated to 90° C. and stirred at this temperature for 15 min. Added to the suspension while stirring was a solution, previously preheated to 90° C., of HAuCl$_4$*3H$_2$O (205 mg) in 8.3 g of water (pH=12.0, adjusted by addition of 20% by weight NaOH). After the addition, the mixture was stirred for a further 30 min, then cooled down and cooled down to room temperature. 1.0 g of NaBH$_4$ was added at RT, and the reaction mixture was stirred for a further 30 min and then filtered. Subsequently, the mixture was washed six times with 50 ml each time of water. The material was dried at 105° C. for 10 h. The PZC of this material was 11.15.

Example 20

A suspension of 10 g of doped support from Example 1 in 33.3 g of demineralized water was heated to 90° C. and stirred at this temperature for 15 min. Added to the suspension while stirring was a solution, previously preheated to 90° C., of HAuCl$_4$*3H$_2$O (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 9.49.

Example 21

A suspension of 10 g of doped support from Example 2 in 33.3 g of demineralized water was heated to 90° C. and stirred at this temperature for 15 min. Added to the suspension while stirring was a solution, previously preheated to 90° C., of HAuCl$_4$*3H$_2$O (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 8.57.

Comparative Example 4

A suspension of 10 g of doped support from Example 3 in 33.3 g of demineralized water was heated to 90° C. and stirred at this temperature for 15 min. Added to the suspension while stirring was a solution, previously preheated to 90° C., of $HAuCl_4*3H_2O$ (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 6.99.

Example 22

A suspension of 10 g of doped support from Example 1 in 33.3 g of demineralized water was heated to 90° C. and stirred at this temperature for 15 min. Added to the suspension while stirring was a solution, previously preheated to 90° C., of $HAuCl_4*3H_2O$ (205 mg) in 8.3 g of water (pH=0.4, adjusted by addition of concentrated hydrochloric acid). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 9.29.

Example 23

A suspension of 10 g of doped support from Example 1 in 33.3 g of demineralized water was heated to 90° C. and stirred at this temperature for 15 min. Added to the suspension while stirring was a solution, previously preheated to 90° C., of $HAuCl_4*3H_2O$ (205 mg) in 8.3 g of water (pH=5.2, adjusted by addition of 20% by weight NaOH solution). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 9.63.

Example 24

A suspension of 10 g of doped support from Example 10 in 33.3 g of demineralized water was heated to 90° C. and stirred at this temperature for 15 min. Added to the suspension while stirring was a solution, previously preheated to 90° C., of $HAuCl_4*3H_2O$ (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 8.80.

Comparative Example 5

A suspension of 10 g of doped support from Example 1 in 33.3 g of demineralized water was heated to 90° C. and stirred at this temperature for 15 min. Added to the suspension while stirring was a solution, previously preheated to 90° C., of $HAuCl_4*3H_2O$ (205 mg) and $Ni(NO_3)_2*6H_2O$ (567 mg, 1.95 mmol) in 8.3 g of water (pH=2.3). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 8.64.

Example 25

A suspension of 10 g of doped support from Example 11 in 33.3 g of demineralized water was heated to 90° C. and stirred at this temperature for 15 min. Added to the suspension while stirring was a solution, previously preheated to 90° C., of $HAuCl_4*3H_2O$ (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 9.69.

Example 26

A suspension of 10 g of doped support from Example 12 in 33.3 g of demineralized water was heated to 90° C. and stirred at this temperature for 15 min. Added to the suspension while stirring was a solution, previously preheated to 90° C., of $HAuCl_4*3H_2O$ (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 9.29.

Example 27

A suspension of 10 g of doped support from Example 13 in 33.3 g of demineralized water was heated to 90° C. and stirred at this temperature for 15 min. Added to the suspension while stirring was a solution, previously preheated to 90° C., of $HAuCl_4*3H_2O$ (205 mg) in 8.3 g of water (pH=1.6). After the addition, the mixture was stirred for a further 30 min, then cooled and filtered at room temperature, and subsequently washed six times with 50 ml each time of water. The material was dried at 105° C. for 10 h, finely crushed with a mortar and pestle, heated from 18° C. up to 450° C. within 1 h and finally calcined at 450° C. for 5 h. The PZC of this material was 9.14.

Examples in a Batch Process for MMA Preparation

A gold-containing catalyst (384 mg), methacrolein (1.20 g) and methanol (9.48 g) were stirred for 2 h in an atmosphere of 7% by volume of $O_2$ in $N_2$ at 60° C. and a pressure of 30 bar in a 140 ml steel autoclave with a magnetic stirrer. After 2 h, the mixture was cooled down, degassed, filtered and analysed by means of gas chromatography (GC). Each catalyst was tested at least twice under identical conditions and the results of the respective experiments were averaged. The resulting conversion of methacrolein (C(MAL) in %), the space-time yield (STY, reported in mol MMA/kg cat.*h) and the selectivity of the conversion of the methacrolein to MMA (S(MMA), in %) for every catalyst tested are collated in Table 1 below.

TABLE 1

(catalyst performance in batch tests after production):

| Ex. | Do-pant | PZC (cat.) | PZC (support) | pH (Au solution) | C(MAL), % | STY, mol MMA/kg cat.*h | S(MMA), % |
|---|---|---|---|---|---|---|---|
| CE2 | Sn | 8.89 | 6.85 | 1.6 | 20.7 | 3.8 | 85.3 |
| 14 | Bi | 9.09 | 9.21 | 1.6 | 42.5 | 8.2 | 91.4 |
| 15 | Mn | 8.72 | 8.95 | 1.6 | 49.4 | 9.4 | 89.7 |
| 16 | Ce | 8.92 | 9.56 | 1.6 | 65.0 | 13.2 | 95.5 |
| 17 | Zr | 8.87 | 8.90 | 1.6 | 37.6 | 7.3 | 90.3 |
| 18 | Pb | 8.59 | 9.35 | 1.6 | 62.4 | 12.5 | 94.2 |
| 19 | Al | 8.82 | 9.12 | 1.6 | 30.7 | 6.3 | 93.1 |
| CE3 | Mg | 11.15 | 9.81 | 12.0 | 20.1 | 3.6 | 92.3 |
| 20 | Mg | 9.49 | 9.81 | 1.6 | 41.7 | 8.5 | 98.6 |
| 21 | Mg | 8.57 | 9.36 | 1.6 | 29.5 | 6.3 | 91.9 |
| CE4 | Mg | 6.99 | 7.91 | 1.6 | 21.2 | 3.9 | 82.3 |
| 22 | Mg | 9.29 | 9.81 | 0.4 | 31.9 | 6.5 | 85.3 |
| 23 | Mg | 9.63 | 9.81 | 5.2 | 34.8 | 7.1 | 92.5 |
| 24 | Y | 8.80 | 9.34 | 1.6 | 43.7 | 8.7 | 92.8 |
| CE5 | Ni | 8.64 | 9.81 | 2.3 | 74.9 | 15.4 | 99.0 |
| 25 | La | 9.69 | 10.20 | 1.6 | 48.8 | 10.1 | 95.7 |
| 26 | Mg | 9.29 | 12.14 | 1.6 | 31.6 | 5.5 | 81.4 |
| 27 | Li | 9.14 | 12.31 | 1.6 | 29.2 | 5.2 | 81.9 |

These examples and comparative example showed that catalysts having too high a PZC value (CE3) or too low a PZC value (CE4) have a lower activity compared to comparable catalysts having a PZC value of the invention (Examples 20 and 21), in the form of a reduced space-time yield (STY). It was also possible to show that a number of metals—as claimed—exhibit good activities and selectivities, whereas, for example, contrary to expectation, tin (CE2) is less suitable and therefore cannot be used in accordance with the invention as component d).

It was also possible to show that catalysts that are in accordance with the invention but have not been prepared by the particularly preferred process likewise according to the invention have poorer properties compared to catalysts produced with preference in accordance with the invention. For instance, in Examples 26 and 27, the PZC value of the support material was too high according to the invention. In both cases, this results in acceptable but non-ideal selectivities and activities of the catalysts. This relationship is especially apparent from a comparison of Example 26 with Example 20. The same applies to the pH of the gold-containing solution. Thus, compared to Example 20 with an ideal value, the catalysts which have been produced with too low (Example 22) or too high (Example 23) a pH give likewise selectivities (Example 22) and activities (Examples 22 and 23) that are acceptable but also in need of improvement.

The initially very good performance of the Ni-containing catalyst known from the literature according to CE5 becomes the opposite when the long-term action of this catalyst is considered (see CE5, Table 2).

Hydrolysis Tests with Gold Catalysts

Examples 28 to 32, Comparative Examples 6 and 7

4 g of a catalyst powder were suspended in 200 g of a 10% by weight sodium acetate solution (pH=7, adjusted by addition of acetic acid) at 80° C. while stirring (500 rpm). Acetic acid was added as required to keep the pH constant at 7. After stirring at 80° C. for 16 h, the catalyst was filtered off, washed with demineralized water and dried in a drying cabinet at 105° C. within 10 h. The (dry) catalyst thus treated was tested in a batch test for MMA preparation as described above. The results of these tests (mean values from two batch tests in each case) are compiled in the table which follows and compared with the batch tests with the fresh catalysts.

TABLE 2

(catalyst performance in batch tests after a hydrolysis test)

| | | Fresh catalyst | | | Treated catalyst | | |
|---|---|---|---|---|---|---|---|
| Ex. | Cat. Ex. | C(MAL), % | STY, mol MMA/kg cat.*h | S(MMA), % | C(MAL), % | STY, mol MMA/kg cat.*h | S(MMA), % |
| CE6 | CE5(Ni) | 74.9 | 15.4 | 99.0 | 8.5 | 1.1 | 59.9 |
| 28 | 16(Ce) | 65.0 | 13.2 | 95.5 | 46.3 | 8.9 | 91.6 |
| 29 | 25(La) | 48.8 | 10.1 | 95.7 | 56.2 | 10.8 | 92.8 |
| 30 | 18(Pb) | 62.4 | 12.5 | 94.2 | 55.9 | 11.2 | 93.5 |
| 31 | 20(Mg) | 41.7 | 8.5 | 98.6 | 40.1 | 8.3 | 93.8 |
| CE7 | 22(Mg) | 31.9 | 6.5 | 85.3 | 23.6 | 4.8 | 85.6 |
| 32 | 23(Mg) | 34.8 | 7.1 | 92.5 | 35.1 | 6.9 | 87.6 |

These experiments showed that the long-term activity of the catalysts of the invention is very good, whereas catalysts according to the prior art containing non-inventive components d), for example Ni (CE5), show a very significant drop in activity and would have to be exchanged again quickly under continuous production conditions.

According to Comparative Example 7, the same applies to catalysts having a non-optimal pH of the gold-containing solution in the catalyst production. These too suffer a high loss of activity in an aqueous medium.

Continuous Test for Preparation of MMA (General Description)

A stirred tank reactor having a total volume of 400 ml was initially charged with 20 g of powder catalyst. The pH of a 42.5% by weight solution of MAL in methanol was adjusted to pH=7 while stirring by the addition of a 1% by weight solution of NaOH in methanol. This solution was fed continuously at a constant rate of addition to the stirred and sparged stirred tank reactor (sparging with air) under pressure of 10 bar and at internal temperature of 80° C. At the same time, a sufficient amount of 1% by weight NaOH solution (in methanol) was fed into this reactor that the value in the reactor remained constant at pH=7. The reaction mixture was withdrawn continuously from the reactor via a filter. After the time specified below, the product samples were taken and analysed by gas chromatography.

Comparative Example 8: Continuous Test for Preparation of MMA with Au/NiO Catalyst In this example, 20 g of the NiO—Au catalyst from Comparative Example 5 (prepared analogously to EP2177267A1 and EP2210664A1) were used in the continuous MMA preparation as described above. The results are compiled in Table 3.

Example 33

In this example, 20 g of a $CeO_2$—Au catalyst of the invention from Example 15 were used in the MMA preparation as described above. The results are compiled in Table 3.

TABLE 3

Continuous MMA preparation with selected catalysts

| Ex. | TOS [h] | Feed [g/h] | C(MAL), % | STY, mol MMA/kg cat. *h | S(MMA), % |
|---|---|---|---|---|---|
| CE5 | 100 | 47.0 | 77.6 | 10.4 | 96.1 |
| CE5 | 1000 | 47.0 | 69.7 | 9.3 | 91.5 |
| 33 | 100 | 55.6 | 68.2 | 10.1 | 96.0 |
| 33 | 1000 | 55.0 | 62.5 | 9.9 | 96.0 |

Finally, comparison in a continuous oxidative esterification can show that, compared to the Ni-containing catalyst as described in the prior art, the selectivity of a catalyst of the invention remains at a constantly high level after 1000 h of operating time, whereas the prior art catalyst loses 4.6% selectivity. The activity of the catalyst of the invention also declines to a much lesser degree within this period.

The invention claimed is:

1. A catalyst, comprising:
   a) 0.01 to 10 mol % of gold,
   b) 40 to 94 mol % of silicon,
   c) 3 to 40 mol % of aluminium, and
   d) 2 to 40 mol % of at least one element selected from the group consisting of alkali metals, alkaline earth metals, lanthanoids having atomic numbers 57 to 71, Y, Sc, Ti, Zr, Cu, Mn, Pb and Bi,
   wherein components b) to d) are present as oxides and the stated amounts of components a) to d) relate to 100 mol % of the composition of the catalyst without oxygen,
   wherein the catalyst is in the form of particles and is capable of catalyzing oxidative esterification of aldehydes to carboxylic esters,
   wherein the catalyst has a shell structure comprising a core and at least one shell, where at least 80% of the total amount of component a) is part of a shell, and
   wherein the catalyst has a PZC value between 7 and 11.

2. The catalyst according to claim 1, which, except for the oxygen, consists of components a) to d).

3. The catalyst according to claim 1, wherein the catalyst comprises between 0.05 and 2 mol % of component a).

4. The catalyst according to claim 1, wherein component a) is in the form of particles having a mean diameter between 2 and 10 nm.

5. The catalyst according to claim 1, wherein the catalyst particles have an average diameter between 10 and 200 μm and a spherical shape.

6. The catalyst according to claim 1, wherein the catalyst comprises between 2 and 30 mol % of Mg, Ce, La, Y, Zr, Mn, Pb and/or Bi as component d).

7. The catalyst according to claim 1, wherein the catalyst has a core and two shells, wherein at least 80% of the total amount of component a) is within an inner shell of the two shells.

8. A process for producing catalyst particles, wherein admixing a basic mixed oxide support with a gold-containing solution to form a component a) having a pH between 0.5 and 5.0,
   wherein the basic mixed oxide support has a PZC value between 8 and 12 and a mean diameter between 10 and 200 μm, consists of b) 40 to 94 mol % of silicon, c) 3 to 40 mol % of aluminium and d) 2 to 40 mol % of at least one element selected from alkali metals, alkaline earth metals, rare earth metals, Ti, Zr, Cu, Mn, Pb and Bi,
   wherein components b) to d) are present as oxides and the stated amounts of components a) to d) relate to 100 mol % of the composition of the catalyst without oxygen.

9. The process according to claim 8, wherein the gold-containing solution contains at least one additional compound including components b), c) and/or d) in ionic form.

10. A method of producing an alkyl (meth)acrylate, comprising:
    reacting (meth)acrolein with oxygen and a monofunctional alcohol to give the alkyl (meth)acrylate;
    wherein the reacting is in the presence of a catalyst according to claim 1.

11. The method according to claim 10, wherein methacrolein is reacted with oxygen and methanol to give MMA.

12. A method of producing a hydroxyalkyl (meth)acrylate or a di-, tri- or tetra(meth)acrylate, comprising:
    reacting (meth)acrolein with oxygen and a di-, tri- or tetrafunctional alcohol to give the hydroxyalkyl (meth)acrylate or to give the di-, tri- or tetra(meth)acrylate;
    wherein the reacting is in the presence of a catalyst according to claim 1.

13. The method according to claim 10, wherein the reacting is conducted continuously.

14. The method according to claim 13, wherein the catalyst is present in suspension form in a stirred reactor during the reacting.

15. The method according to claim 12, wherein the reacting is conducted continuously.

16. The method according to claim 15, wherein the catalyst is present in suspension form in a stirred reactor during the reacting.

17. The catalyst according to claim 3, wherein component a) is in the form of particles having a mean diameter between 2 and 10 nm.

18. The catalyst according to claim 3, wherein the catalyst particles have an average diameter between 10 and 200 μm and a spherical shape.

19. The catalyst according to claim 3, wherein the catalyst comprises between 2 and 30 mol % of Mg, Ce, La, Y, Zr Mn, Pb and/or Bi as component d).

20. The catalyst according to claim 3, wherein the catalyst has a core and two shells, wherein at least 80% of the total amount of component a) is within an inner shell of the two shells.

* * * * *